US00PP35589P2

(12) United States Plant Patent
Barnes et al.

(10) Patent No.: US PP35,589 P2
(45) Date of Patent: Jan. 16, 2024

(54) PETUNIA PLANT NAMED 'WNPETMVSS23'

(50) Latin Name: ***Petunia* X *hybrida***
Varietal Denomination: WNPETMVSS23

(71) Applicants: Brent D. Barnes, Riverside, CA (US); Adam Moseley, Kyle, TX (US)

(72) Inventors: Brent D. Barnes, Riverside, CA (US); Adam Moseley, Kyle, TX (US)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 18/129,033

(22) Filed: Mar. 30, 2023

(51) Int. Cl.
*A01H 5/02* (2018.01)
*A01H 6/82* (2018.01)

(52) U.S. Cl.
USPC ..... Plt./356.22
CPC ..... *A01H 6/824* (2018.05)

(58) Field of Classification Search
USPC ..... Plt./356.22, 356.17, 356.18, 356.19, Plt./356.2, 356.21
CPC ..... A01H 5/02
See application file for complete search history.

*Primary Examiner* — Kent L Bell
(74) *Attorney, Agent, or Firm* — C. Anne Whealy

(57) ABSTRACT

A new and distinct *Petunia* plant named 'WNPETMVSS23', characterized by its upright to outwardly spreading and mounding to eventually trailing and decumbent plant habit; vigorous growth habit and rapid growth rate; freely branching habit; dense and bushy plant form; early and freely flowering habit; single-type flowers that are reddish purple in color; and excellent container and garden performance.

2 Drawing Sheets

Figure 1:
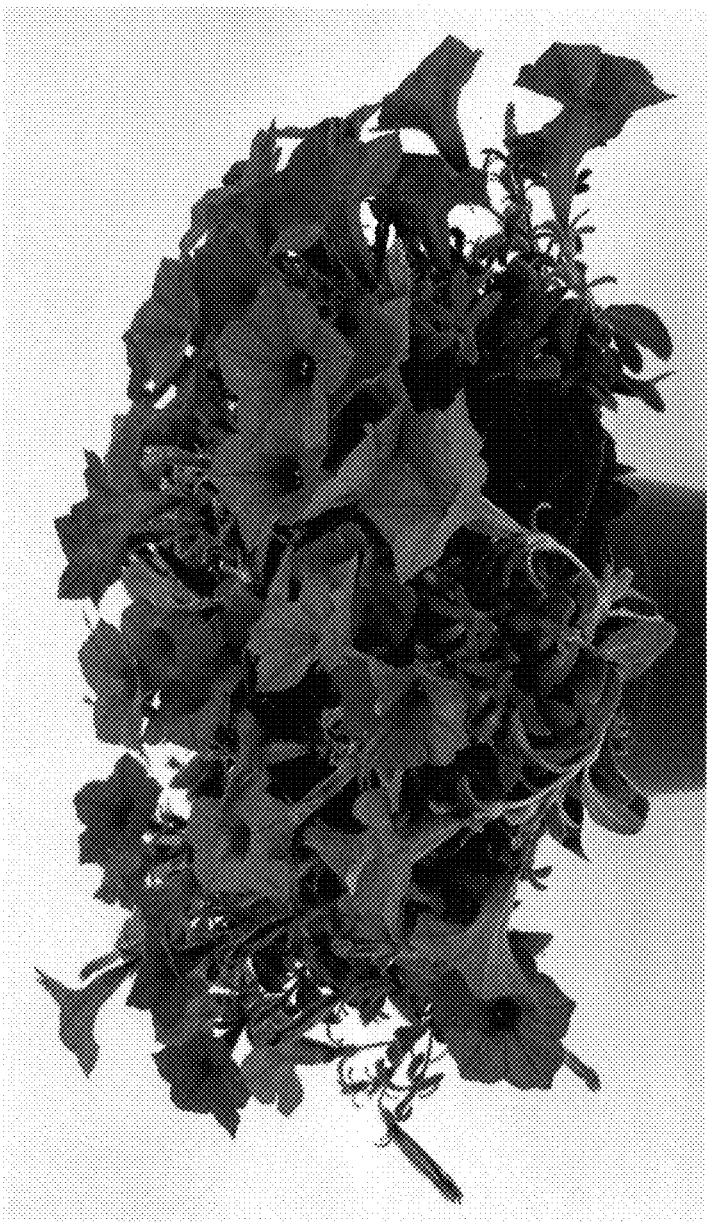

Botanical designation: *Petunia* X *hybrida.*
Cultivar denomination: 'WNPETMVSS23'.

BACKGROUND OF THE INVENTION

The present invention relates to a new and distinct cultivar of *Petunia* plant, botanically known as *Petunia* X *hybrida* and hereinafter referred to by the name 'WNPETMVSS23'.

The new *Petunia* plant is a product of a planned breeding program conducted by the Inventors in Bonsall, California and Tyler, Texas. The objective of the breeding program is to create new vigorous, freely-branching and uniformly mounding *Petunia* plants with early and freely flowering habit, attractive flowers and good garden performance.

The new *Petunia* plant originated from a cross-pollination made by the Inventors on Oct. 15, 2019 in Bonsall, California of a proprietary selection of *Petunia* X *hybrida* identified as code number PS001*001, not patented, as the female, or seed, parent with a proprietary selection of *Petunia* X *hybrida* identified as code number 17PB276-01, not patented, as the male, or pollen, parent. The new *Petunia* plant was discovered and selected by the Inventors as a single flowering plant within the progeny of the stated cross-pollination in a controlled greenhouse environment in Tyler, Texas on Oct. 5, 2020.

Asexual reproduction of the new *Petunia* plant by vegetative terminal cuttings in a controlled greenhouse environment in Tyler, Texas since Oct. 12, 2020 has shown that the unique features of this new *Petunia* plant are stable and reproduced true to type in successive generations.

SUMMARY OF THE INVENTION

Plants of the new *Petunia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNPETMVSS23'. These characteristics in combination distinguish 'WNPETMVSS23' as a new and distinct *Petunia* plant:

1. Upright to outwardly spreading and mounding to eventually trailing and decumbent plant habit.
2. Vigorous growth habit and rapid growth rate.
3. Freely branching habit; dense and bushy plant form.
4. Early and freely flowering habit.
5. Single-type flowers that are reddish purple in color.
6. Excellent container and garden performance.

Plants of the new *Petunia* can be compared to plants of the female parent selection. In side-by-side comparisons, plants of the new *Petunia* differ primarily from plants of the female parent selection in the following characteristics:

1. Plants of the new *Petunia* are shorter and denser than plants of the female parent selection.
2. Plants of the new *Petunia* are not as vigorous as plants of the female parent selection.
3. Plants of the new *Petunia* have smaller flowers than plants of the female parent selection.
4. Flowers of plants of the new *Petunia* are reddish purple in color whereas flowers of plants of the female parent selection are pinkish purple in color.

Plants of the new *Petunia* can be compared to plants of the male parent selection. In side-by-side comparisons, plants of the new *Petunia* differ primarily from plants of the male parent selection in the following characteristics:

1. Plants of the new *Petunia* are more trailing than plants of the male parent selection.

2. Flowers of plants of the new *Petunia* are reddish purple in color whereas flowers of plants of the male parent selection are bluish purple in color.

Plants of the new *Petunia* can be compared to plants of *Petunia* X *hybrida* 'USTUN2401M', disclosed in U.S. Plant Pat. No. 29,664. In side-by-side comparisons, plants of the new *Petunia* differ primarily from plants of 'USTUN2401M' in the following characteristics:

1. Plants of the new *Petunia* are more trailing than and not as spreading as plants of 'USTUN2401M'.
2. Plants of the new *Petunia* have smaller flowers than plants of 'USTUN2401M'.
3. Flowers of plants of the new *Petunia* are reddish purple in color whereas flowers of plants of 'USTUN2401M' are hot pink in color.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph on the first sheet (FIG. 1) is a side perspective view of a typical flowering plant of 'WNPETMVSS23' grown in a container.

Figure 2:
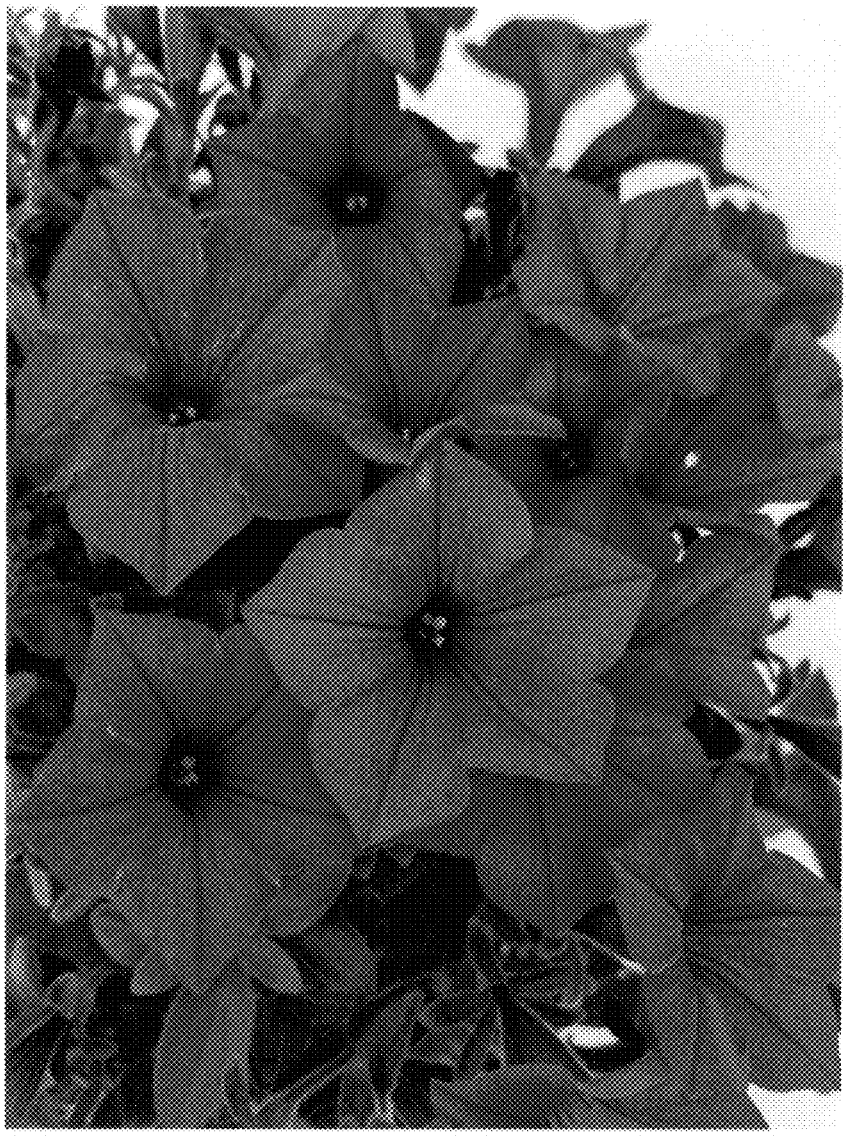

The photograph on the second sheet (FIG. 2) is a close-up view of a typical flowering plant of 'WNPETMVSS23'.

DETAILED BOTANICAL DESCRIPTION

The aforementioned photographs and following observations and measurements describe plants grown during the summer in 740-ml containers in an acrylic-covered greenhouse in Carlton, Michigan and under cultural practices typical of commercial *Petunia* production. During the production of the plants, day temperatures ranged from 18C to 32C and night temperatures ranged from 18C to 24C. Plants were pinched two weeks after planting and were five weeks from planting rooted cuttings when the photographs and description were taken. In the following description, color references are made to The Royal Horticultural Society Colour Chart, 2015 Edition, except where general terms of ordinary dictionary significance are used.

Botanical classification: *Petunia* X *hybrida* 'WNPETMVSS23'.

Parentage:

*Female, or seed, parent.*—Proprietary selection of *Petunia* X *hybrida* identified as code number PS001*001, not patented.

*Male, or pollen, parent.*—Proprietary selection of *Petunia* X *hybrida* identified as code number 17PB276-01, not patented.

Propagation:

*Type.*—Terminal vegetative cuttings.

*Time to initiate roots, summer.*—About three to four days at ambient temperatures about 28C.

*Time to initiate roots, winter.*—About five to seven days at ambient temperatures about 20C.

*Time to produce a rooted plant, summer.*—About three or four weeks at ambient temperatures about 28C.

*Time to produce a rooted plant, winter.*—About four to five weeks at ambient temperatures about 20C.

*Root description.*—Fine, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Upright to outwardly spreading and mounding to eventually trailing and decumbent plant habit; freely branching habit with about eight to twelve primary lateral branches with secondary laterals developing potentially at every node, dense and bushy plant form; pinching enhances development of lateral branches; vigorous growth habit and rapid growth rate.

*Plant height.*—About 13.5 cm.

*Plant diameter* (*area of spread*).—About 24 cm by 27 cm.

*Lateral branches.*—Length: About 12.5 cm. Diameter: About 1.25 mm to 1.5 mm. Internode length: About 1.3 cm to 1.5 cm. Strength: Strong; flexible, not brittle. Aspect: Initially arching upwardly and eventually trailing. Texture and luster: Densely pubescent; slightly glossy. Color, developing and developed: Close to 144A.

Leaf description:

*Arrangement.*—Alternate before flowering; opposite after flowers develop; leaves simple.

*Length.*—About 3.5 cm to 4 cm.

*Width.*—About 1.4 cm to 1.6 cm.

*Shape.*—Elliptic with obovate tendencies.

*Apex.*—Acute.

*Base.*—Cuneate.

*Margin.*—Entire, not undulate.

*Texture and luster, upper and lower surfaces.*—Slightly pubescent, pubescence, minute; slightly glossy.

*Venation pattern.*—Pinnate, arcuate.

*Color.*—Developing leaves, upper surface: Close to between 146A and 147A. Developing leaves, lower surface: Close to 146A to 146B. Fully developed leaves, upper surface: Close to 147A; venation, close to between 146A and 147A. Fully developed leaves, lower surface: Close to 146A; venation, close to 146A to 146B.

*Petioles.*—Length: About 1 cm. Diameter: About 2.5 mm to 3 mm. Strength: Moderately strong, flexible. Texture and luster, upper and lower surfaces: Slightly pubescent; slightly glossy. Color, upper and lower surfaces: Close to 146A.

Flower description:

*Flower type and flowering habit.*—Single terminal and axillary salverform flowers; flowers face mostly upward to slightly outwardly; freely flowering habit with about 75 developing flowers and open flowers per plant.

*Natural flowering season.*—Long day responsive; long flowering period, plants flower from early spring until frost in the autumn, flowering continuous during this period; early flowering habit, plants begin flowering about four weeks after planting rooted young plants.

*Flower longevity on the plant.*—Depending on temperature, about one to two weeks; petals not persistent, and sepals, persistent.

*Fragrance.*—None detected.

*Flower buds, before showing petal color.*—Length: About 8 mm. Diameter: About 3 mm. Shape: Oblong, elongate. Texture and luster: Pubescent; slightly glossy. Color, developing sepals: Close to 144A to 144B.

*Flower diameter.*—About 3.3 cm to 3.5 cm.

*Flower depth* (*height*).—About 3.4 cm.

*Throat diameter.*—About 7 mm.

*Tube length.*—About 2.2 cm.

*Tube diameter, distally.*—About 7.5 mm.

*Tube diameter, proximally.*—About 1 mm to 1.25 mm.

*Petals.*—Quantity and arrangement: Five petals fused in a single salverform in whorl. Petal lobe length (from throat): About 1.6 cm to 1.8 cm. Petal lobe width: About 1.4 cm to 1.6 cm. Petal lobe shape: Roughly spatulate. Petal lobe apex: Acute. Petal lobe margin: Entire; slightly undulate. Petal lobe texture and luster, upper surface: Smooth, glabrous; velvety; slightly glossy; irridescent. Petal lobe texture and luster, lower surface: Smooth, glabrous along the venation; matte to slightly glossy. Throat texture and luster: Smooth, glabrous; moderately glossy. Tube texture and luster: Moderately to densely pubescent; matte to slightly glossy. Color: When opening, upper surface: Close to NN74A. When opening, lower surface: Close to 75A. Fully opened, upper surface: Close to NN74A; primary venation, close to NN78A, and lateral venation, close to NN74A; color becoming closer to N78A with subsequent development. Fully opened, lower surface: Close to 75A variably tinged with close to NN78A; primary venation, close to 148A, and lateral venation, close to 75A variably tinged with close to NN78A; color becoming closer to 77B to 77C with subsequent development. Flower throat (inside): Close to N75A variably tinged with close to NN78A; venation, close to N78A. Flower tube (outside): Close to 77A; venation, close to 148A tinged with close to 77A.

*Sepals.*—Quantity and arrangement: Five sepals fused in a single star-shaped whorl. Calyx length: About 1.3 cm to 1.5 cm. Calyx diameter: About 3 mm to 3.5 mm. Length: About 1.3 cm to 1.5 cm. Width: About 2 mm to 3 mm. Shape: Linear. Apex: Acute. Margin: Entire. Texture and luster, upper surface: Sparsely to moderately pubescent; slightly glossy. Texture and luster, lower surface: Moderately pubescent; slightly glossy. Color: When opening and fully developed, upper surface: Close to between 144A and 146A. When opening and fully developed, lower surface: Close to 144A.

*Peduncles.*—Length: About 1.5 cm to 1.75 cm. Width: About 2 mm. Strength: Moderately strong to strong; wiry and flexible, not brittle. Angle: About 30 to 45 degrees from the stem axis. Texture and luster: Densely pubescent; slightly glossy. Color: Close to 144A.

*Reproductive organs.*—Stamens: Quantity per flower: About five. Filament length: About 1.8 cm. Filament color: Close to 145C to 145D. Anther length: About 1.25 mm. Anther shape: Bi-lobed. Anther color: Close to 94B. Pollen amount: Scarce. Pollen color: Close to 91A. Pistils: Quantity per flower: One. Pistil length: About 1.5 cm. Style length: About 1.4 cm. Style color: Distally, close to 145A, and proximally, close to 145C. Stigma diameter: Less than 1 mm. Stigma shape: Round. Stigma color: Close to 148A. Ovary color: Close to 144A.

*Seeds and fruits.*—To date, seed and fruit development has not been observed on plants of the new *Petunia*.

Pathogen & pest resistance: To date, plants of the new *Petunia* have not been noted to be resistant to pathogens or pests common to *Petunia* plants.

Garden performance: Plants of the new *Petunia* have been observed to have excellent garden performance and have been observed to tolerate rain, wind and temperatures ranging from about 1C to about 35C.

It is claimed:

1. A new and distinct *Petunia* plant named 'WNPETMVSS23' as illustrated and described.

* * * * *